US00PP13934P39

(12) United States Plant Patent
Murakami

(10) Patent No.: US PP13,934 P3
(45) Date of Patent: Jul. 1, 2003

(54) NIEREMBERGIA PLANT NAMED 'SUNNICOBU'

(75) Inventor: Yasuyuki Murakami, Shiga (JP)

(73) Assignee: Suntory Limited, Osaka (JP)

( * ) Notice: Subject to any disclaimer, the term of this patent is extended or adjusted under 35 U.S.C. 154(b) by 14 days.

(21) Appl. No.: 09/334,501

(22) Filed: Jun. 17, 1999

(65) Prior Publication Data

US 2003/0033649 P1 Feb. 13, 2003

(51) Int. Cl.[7] ..... A01H 5/00
(52) U.S. Cl. ..... Plt./263
(58) Field of Search ..... Plt./263

(56) References Cited

PUBLICATIONS

UPOV CD–ROM, PBR 10291, JP, Nierembergia named 'Sunnicobu', 1997.*
UPOV CD–ROM, PBR 000005, QZ, Nierembergia named 'Sunnicobu', 2000.*
'Nierembergia' entry from vol. 7 (Ma–Par) of *The New York Botanical Garden Illustrated Encyclopedia of Horticulture*, Thomas H. Everett, ed., Garland Publishing, Inc., New York, pp. 2326–2327. (1981).
'Nierembergia' entry from vol. III (Je–Pt) of *The Royal Horticultural Society Dictionary of Gardening: A Practical and Scientific Encyclopedia of Horticulture*, Fred J. Chittenden, ed., Oxford at the Clarendon Press, p. 1372. (1992).
'Nierembergia' entry from *Hortus Third: A Concise Dictionary of Plants Cultivated in the United States and Canada*, Macmillan Publishing Company, New York (1976) p. 767.
* cited by examiner

*Primary Examiner*—Bruce R. Campell
*Assistant Examiner*—Michelle Kizilkaya
(74) *Attorney, Agent, or Firm*—Burns, Doane, Swecker & Mathis, L.L.P.

(57) ABSTRACT

Disclosed herein is new Nierembergia plant named 'Sunnicobu', having a compact and tufted habit with long internode stem. The stem color varies from grayish olive to grayish brown. Flowers are single and small. The petal is light purple with moderate purple center portion. The bottom color of the corolla throat is vivid yellow and the outside color of corolla tube is pale yellow green. The plant has a high resistance to rain, heat, diseases especially powdery mildew.

2 Drawing Sheets

BOTANICAL/COMMERCIAL CLASSIFICATION

Figure 1:
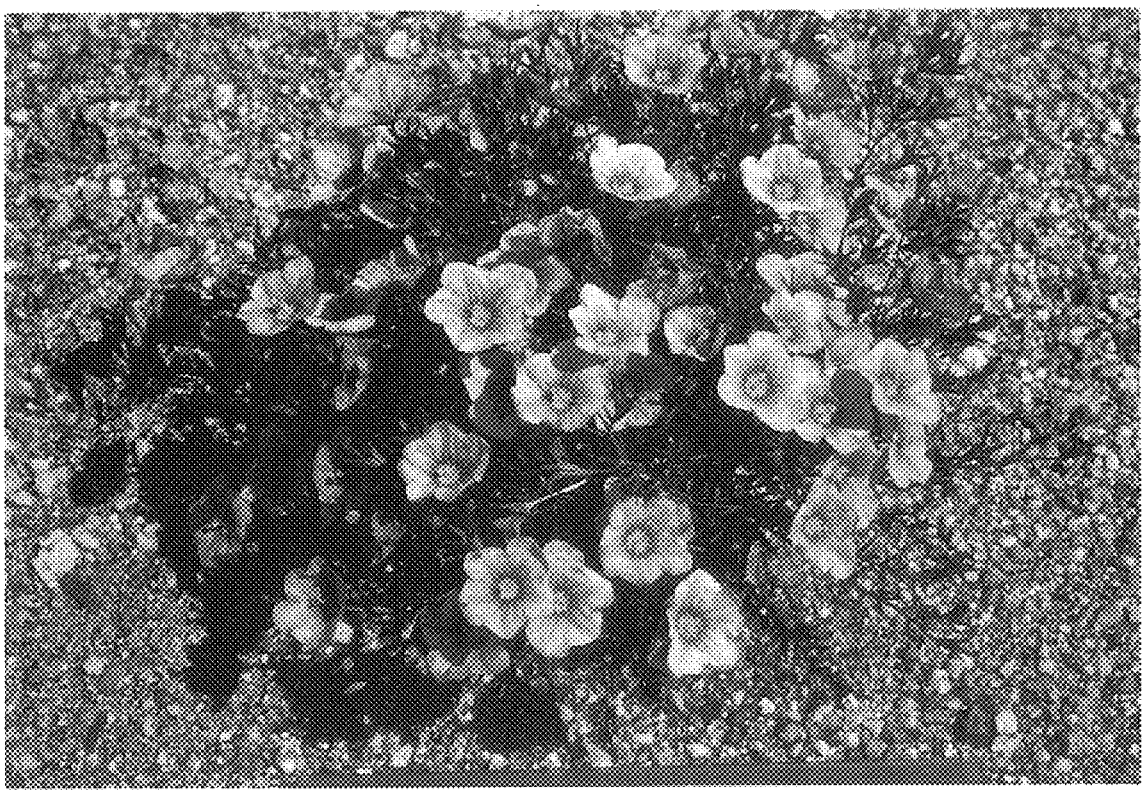

*Nierembergia hybrida/Nierembergia* Plant.

VARIETAL DENOMINATION

'Sunnicobu'.

BACKGROUND OF THE NEW VARIETY

The present invention relates to a new and distinct variety of Nierembergia plant named 'Sunnicobu'. 'Sunnicobu' is the first vegetative propagated variety which was developed by specific hybridization, between *Niembergia gracilis* and *Nierembergia caerulea*. This variety is a breakthrough in breeding, as it combines flowers of light purple with darker center. This variety is compact and tufted habit. It has good winter hardiness, and high resistance to heat, rain, and diseases especially powdery mildew.

Plants in the Nierembergia genus are Solanaceae and herbaceous perennials or semi-woody shrubs and are hardy or half-hardy and flower in long days of the summer. There are 30 species in Mexico to South America, around Chile and Argentina. These plants have stems hanging down or lying flat or erect and have simple leaves. The phyllotaxy is alternate or dispersed. These plants have axillary flowers and have inflorescence type with flower solitary or cyme. The flower color is white, light purple or unusually purple and the shape is funnel-form, campanulate or salver-form. Occasionally the center color is purple. The bottom color of the corolla throat is yellow. Calyx is tubular or funnel-shaped. The tube is thin and the throat spreads widely. The rim separates into 5. There are 5 stamens attached to the tube's inside with 4 of the stamens forming pairs and the remaining one is a small staminode. The capsule has 2 carpels and are split open. The chromosomal number is X=9.

The female parent (non-patented in the United States) used in the crossing of 'Sunnicobu' was *Nierembergia gracilis*, which is a wild species of Nierembergia plant native to Argentina and introduced to Japan in 1992. It is a compact and tufted bush. The flowers are single, medium to small size and white petals. The leaf is lanceolate. *Nierembergia gracilis* is sensitive to rain, heat, and powdery mildew.

The pollen parent (non-patented in the United States) used in the crossing of 'Sunnicobu' was *Nierembergia caerulea*, which is a wild species of Nierembergia genus and cultivated in England and introduced to Japan in 1992. It is erect habit with less branching. The flowers are single, medium size and have vivid purple petals. The leaf is lanceolate and waving. *Nierembergia caerulea* has good winter hardiness and a resistance to rain, diseases and pests.

First of all, two wild types of Nierembergia genus, *Nierembergia gracilis* and *Nierembergia caerulea*, were introduced to Japan in 1992. The seedlings of both wild types Nierembergia genus were grown in Japan since the spring of 1994, and a few seedlings were selected from both lines. Under green-house condition, controlled crossing with seedlings of *Nierembergia gracilis* (♀) and that of *Nierembergia caerulea* (♂) was conducted in June 1995. From seedlings which were obtained through this crossing, 10 seedlings were selected in view of compact and tufted plant habit and flower color in the spring of 1996 in greenhouse condition.

The botanical characteristics of the finally selected 10 varieties were then examined. They were tested at Youkaichi-shi, Shiga-ken, Japan from spring to autumn in 1996. As a result, one variety was selected which met our criteria and was uniform and stable in its characteristics. This new variety of Nierembergia genus plant was named 'Sunnicobu' (*Nierembergia hybrida*).

These wild type of Nierembergia genes plants, *Nierembergia gracilis* and *Nierembergia caerulea*, and 'Sunnicobu' are presently maintained at Youkaichi-shi, Shiga-ken, Japan.

In the following description, the color-coding is in accordance with The Horticultural Color Chart of The Royal Horticultural Society, London, England (R.H.S. Color Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The botanical characteristics of the female parent plant *Nierembergia gracilis* used in the crossing of 'Sunnicobu' are as follows.

Plant:
- *Growth habit.*—Tufted.
- *Height.*—12 cm.
- *Spread.*—26 cm.

Stem:
- *Thickness.*—0.9 mm.
- *Color.*—Moderate olive green (R.H.S. 147A, J.H.S. 3508).
- *Branching.*—Abundant.
- *Pubescence.*—Present.
- *Length of internode.*—8 mm.

Leaf:
- *Whole shape.*—Lanceolate.
- *Apex shape.*—Acuminate.
- *Base shape.*—Cuneate.
- *Length.*—25 mm.
- *Width.*—1.9 mm.
- *Thickness.*—0.3 mm.
- *Color of upper side.*—Moderate yellow green (R.H.S. 137B, J.H.S. 3712).
- *Color of reverse side.*—Moderate yellow green (R.H.S. 138A, J.H.S. 3513).
- *Pubescence.*—Sparse.
- *Attachment angle to stem.*—Horizontal.

Flower:
- *Facing direction.*—Upward.
- *Type.*—Single.
- *Shape.*—Rotate, five-fissured limb.
- *Shape of petal tip.*—Obtuse.
- *Waving of petal.*—Weak.
- *Lobation of petal.*—Shallow.
- *Diameter of petal.*—30 mm.
- *Diameter of tube.*—0.8 mm.
- *Length of tube.*—14 mm.
- *Color of petal.*—White (R.H.S. 155D, J.H.S. –01) with light purple center portion (R.H.S. 85C, J.H.S. 8303).
- *Bottom color of corolla throat.*—Vivid yellow (R.H.S. 12A, J.H.S. 2506).
- *Outside color of corolla throat.*—Pale yellow(R.H.S. 4D, J.H.S. 3303).
- *Flowering habit.*—The earliness of flowering is average for Nierembergia genus.

Pistil:
- *Number.*—1.
- *Color of stigma.*—Strong yellow green (R.H.S. 144A, J.H.S. 3507).

Stamen:
- *Number.*—5.
- *Type.*—Syngenesious.
- *Color of anther.*—Vivid yellow (R.H.S. 12A, J.H.S. 2506).

Hardiness:
- *Winter.*—Good.
- *Rain.*—Poor.
- *Heat.*—Poor.

Resistance:
- *Disease.*—Poor.
- *Insect.*—Excellent.

The botanical characteristics of the male parent plant *Nierembergia caerulea* used in the crossing of 'Sunnicobu' are as follows.

Plant:
- *Growth habit.*—Upright.
- *Height.*—15 cm.
- *Spread.*—18 cm.

Stem:
- *Thickness.*—0.7 mm.
- *Color.*—Moderate olive green (R.H.S. 147A, J.H.S. 3508).
- *Branching.*—Medium.
- *Pubescence.*—Present.
- *Length of internode.*—9 mm.

Leaf:
- *Whole shape.*—Lanceolate.
- *Apex shape.*—Acuminate.
- *Base shape.*—Cuneate.
- *Length.*—15 mm.
- *Width.*—1.6 mm.
- *Thickness.*—0.3 mm.
- *Color of upper side.*—Moderate yellow green (R.H.S. 137A, J.H.S. 3712).
- *Color of reverse side.*—Moderate yellow green (R.H.S. 137B, J.H.S. 3712).
- *Pubescence.*—Sparse.
- *Attachment angle to stem.*—Upright.

Flower:
- *Facing direction.*—Upward.
- *Type.*—Single.
- *Shape.*—Rotate, five-fissured limb.
- *Shape of petal tip.*—Obtuse.
- *Waving of petal.*—Weak.
- *Lobation of petal.*—Shallow.
- *Diameter of petal.*—33 mm.
- *Diameter of tube.*—0.8 mm.
- *Length of tube.*—16 mm.
- *Color of petal.*—Vivid purple (R.H.S. 88A, J.H.S. 8306).
- *Bottom color of corolla throat.*—Brilliant greenish yellow (R.H.S. 9B, J.H.S. 2704).
- *Outside color of corolla throat.*—Light gray (R.H.S. 202C, J.H.S. –2).
- *Flowering habit.*—Late.

Pistil:
- *Number.*—1.
- *Color of stigma.*—Strong yellow green (R.H.S. 144A, J.H.S. 3507).

Stamen:
*Number.*—5.
*Type.*—Syngenesious.
*Color of anther.*—Vivid yellow (R.H.S. 12A, J.H.S. 2506).
Hardiness:
*Winter.*—Excellent.
*Rain.*—Excellent.
*Heat.*—Good.
Resistance:
*Disease.*—Excellent.
*Insect.*—Excellent.

The botanical characteristics of the similar variety 'Montebranco' used for examination as a comparison are as follows.

Plant:
*Growth habit.*—Tufted.
*Height.*—9 cm.
*Spread.*—18 cm.
Stem:
*Thickness.*—0.8 mm.
*Color.*—Moderate olive green (R.H.S. 146A, J.H.S. 3508).
*Branching.*—Abundant.
*Pubescence.*—Present.
*Length of internode.*—8 mm.
Leaf:
*Whole shape.*—Linear.
*Apex shape.*—Acuminate.
*Base shape.*—Cuneate.
*Length.*—15 mm.
*Width.*—1.1 mm.
*Thickness.*—0.3 mm.
*Color of upper side.*—Moderate yellow green (R.H.S. 138A, J.H.S. 3513).
*Color of reverse side.*—Moderate yellow green (R.H.S. 137C, J.H.S. 3712).
*Pubescence.*—Sparse.
*Attachment angle to stem.*—Horizontal.
Flower:
*Facing direction.*—Upward.
*Type.*—Single.
*Shape.*—Rotate, five-fissured limb.
*Shape of petal tip.*—Obtuse.
*Waving of petal.*—Weak.
*Lobation of petal.*—Shallow.
*Diameter of petal.*—27 mm.
*Diameter of tube.*—0.8 mm.
*Length of tube.*—15 mm.
*Color of petal.*—White (R.H.S. 155D, J.H.S. –01).
*Bottom color of corolla throat.*—Vivid yellow (R.H.S. 12A, J.H.S. 2506).
*Outside color of corolla throat.*—Pale yellow green (R.H.S. 4D, J.H.S. 3303).
*Flowering habit.*—The earliness of flowering is average for Nierembergia genus.
Pistil:
*Number.*—1.
*Color of stigma.*—Strong yellow green (R.H.S. 144A, J.H.S. 3507).
Stamen:
*Number.*—5.
*Type.*—Syngenesious.
*Color of anther.*—Vivid yellow (R.H.S. 12A, J.H.S. 2506).
Hardiness:
*Winter.*—Good.
*Rain.*—Poor.
*Heat.*—Poor.
Resistance:
*Disease.*—Poor.
*Insect.*—Excellent.

This new and distinct variety of Nierembergia plant, 'Sunnicobu', was asexually reproduced by cutting at Oomori-cho, Youkaichi-shi, Shiga-ken, Japan and the homogeneity and stability thereof were confirmed.

SUMMARY OF THE NEW VARIETY

The stem of 'Sunnicobu' is 0.9 mm in diameter, medium size in its group, and has upright growth habit. The stem is flexible, therefore it extends laterally and new stems appear from the center. Due to that habit, plant has a medium sized round shape, averaging 10 cm in height and 15 cm in width at the blooming time of the 5th to the 10th flower. The stem color varies from grayish olive (R.H.S. 152B, J.H.S. 2917) to grayish brown (R.H.S. 200C, J.H.S. 1619) as against the stem of 'Montebranco' which shows no anthocyanin coloration and moderate olive green. The stem has sparse white pubescence, and the pubescence is slightly denser than that of 'Montebranco'.

The number of the first lateral branches is about 6, and the number of the second lateral branches is about 3 at the blooming time of the 5th to the 10th flower, which is similar to that of 'Montebranco'. Internode is 13 mm at the blooming time of the first flower. The internode is longer than that of 'Montebranco'.

The leaves of 'Sunnicobu' are lanceolate, 21 mm long, 2 mm width, and 0.4 mm thickness. The leaf size is larger than that of 'Montebranco'.

The flowers of 'Sunnicobu' face upward. The corolla tube is very narrow, 16 mm length (from sepal to petal) and 0.8 mm in diameter. The very narrow corolla tube is characteristic of the Nierembergia genus. The flower is single and the flower is 33 mm in diameter. Petal color is light purple (R.H.S. 85B, J.H.S. 8303) with moderate purple (R.H.S. 86D, J.H.S. 8309) center portion. That is a distinctive characteristic of this new variety, 'Sunnicobu'. Bottom color of corolla throat is vivid yellow (J.H.S. 2506, R.H.S. 9A, 9B, 12A, 13A). Flower-stem is 9 mm long and 0.5 mm wide, and longer and thicker than that of 'Montebranco'. The flower structure of 'Sunnicobu' is the same as the varieties of this Nierembergia genus. The flowering duration of 'Sunnicobu' is six months, with a blooming period extending from May to October when planted in April in Japan. About 100 flowers per plant bloom at once. An individual bloom commonly lasts 3 to 5 days.

It has good winter hardiness and can survive at –10° C. Also it has higher resistance to heat and rain than 'Montebranco'. However, some damage to flower petals occurs under heavy rain due to its thinness, which is characteristic of the Nierembergia genus. It has high resistance to powdery mildew and is almost not damaged by diseases and pests.

BRIEF DESCRIPTION OF THE PHOTOGRAPHS

Figure 2:
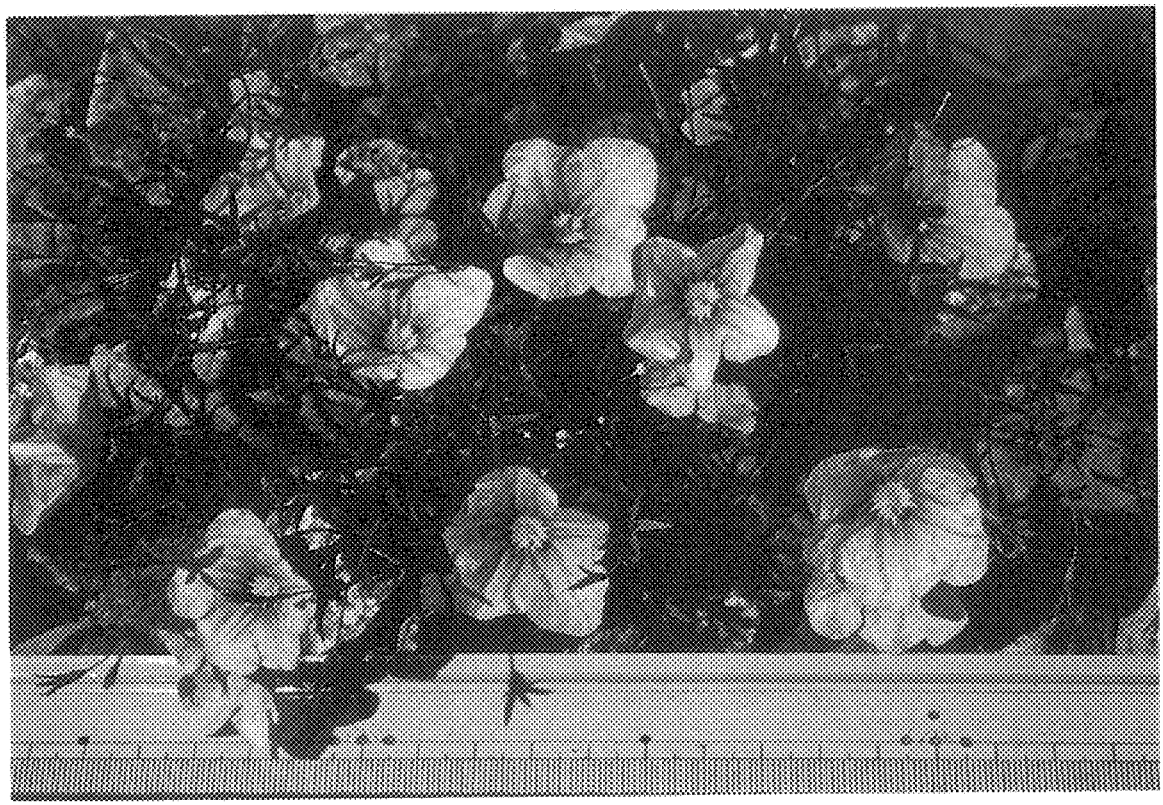

FIG. 1 is a photograph giving a partial view of the new variety of Nierembergia plant 'Sunnicobu' planted in the ground; and FIG. 2 is a photograph of flowers of the new variety of Nierembergia plant 'Sunnicobu'.

DESCRIPTION OF THE NEW VARIETY

The botanical characteristics of this new and distinct variety of Nierembergia plant named 'Sunnicobu' are as follows.

Plant:
- *Growth habit.*—Tufted.
- *Height.*—10 cm.
- *Spread.*—28 cm.

Stem:
- *Thickness.*—0.9 mm.
- *Color.*—Grayish olive to Grayish brown (R.H.S. 152B to 200C, J.H.S. 2917 to 1619).
- *Branching.*—Abundant.
- *Pubescence.*—Dense.
- *Length of internode.*—13 mm.

Leaf:
- *Whole shape.*—Lanceolate.
- *Aex shape.*—Acuminate.
- *Base shape.*—Cuneate.
- *Length.*—21 mm.
- *Width.*—2.0 mm.
- *Thickness.*—0.4 mm.
- *Color of upper side.*—Moderate yellow green (R.H.S. 137B, J.H.S. 3712).
- *Color of reverse side.*—Moderate yellow green (R.H.S. 137C, J.H.S. 3712).
- *Pubescence.*—Sparse.
- *Attachment angle to stem.*—Upright.

Flower:
- *Facing direction.*—Upward.
- *Type.*—Single.
- *Shape.*—Rotate, five-fissured limb.
- *Shape of petal tip.*—Obtuse.
- *Waving of petal.*—Weak.
- *Lobation of petal.*—Shallow.
- *Diameter of petal.*—33 mm.
- *Diameter of tube.*—0.8 mm.
- *Length of tube.*—16 mm.
- *Color of petal.*—Light purple (R.H.S. 85B, J.H.S. 8303) with moderate purple center portion (R.H.S. 86D, J.H.S. 8309).
- *Bottom color of corolla throat.*—Vivid yellow (R.H.S. 12A, J.H.S. 2506).
- *Outside color of corolla throat.*—Pale yellow green (R.H.S. 157A, J.H.S. 3303).
- *Flowering habit.*—When planted in April in Japan, the blooming period extends from May to October. The earliness of flowering is average for Nierembergia genus.

Pistil:
- *Number.*—1.
- *Color of stigma.*—Strong yellow green — (R.H.S. 144A, J.H.S. 3507).

Stamen:
- *Number.*—5.
- *Type.*—Syngenesious.
- *Color of anther.*—Vivid yellow (R.H.S. 12A, J.H.S. 2506).

Hardiness:
- *Winter.*—Excellent.
- *Rain.*—Excellent.
- *Heat.*—Excellent.

Resistance:
- *Disease.*—Excellent.
- *Insect.*—Excellent.

This new variety of Nierembergia plant 'Sunnicobu' is most suitable for flower bedding and potting, and also excellent for ground cover.

I claim:

1. A new and distinct variety of Nierembergia plant named 'Sunnicobu', substantially as herein illustrated and described.

* * * * *